United States Patent
Annecke

(10) Patent No.: US 7,276,023 B2
(45) Date of Patent: Oct. 2, 2007

(54) DEVICE FOR CHECKING ENDOSCOPE CHANNELS

(75) Inventor: Karl Heinz Annecke, Bensheim (DE)

(73) Assignee: BHT Hygienetechnik GmbH, Gersthofen (DE)

( * ) Notice: Subject to any disclaimer, the term of this patent is extended or adjusted under 35 U.S.C. 154(b) by 0 days.

(21) Appl. No.: 10/926,553

(22) Filed: Aug. 25, 2004

(65) Prior Publication Data

US 2006/0047186 A1   Mar. 2, 2006

(51) Int. Cl.
*A61B 1/00* (2006.01)

(52) U.S. Cl. ............ 600/101; 600/133; 600/156; 600/158; 73/1.57; 73/1.58; 73/1.73; 73/37; 422/3; 422/28; 134/22.11; 134/212.12

(58) Field of Classification Search ........... 600/101, 600/158; 422/3, 28; 73/1.57
See application file for complete search history.

(56) References Cited

U.S. PATENT DOCUMENTS

| | | | |
|---|---|---|---|
| 3,271,993 A | | 9/1966 | Whitson |
| 4,395,918 A | | 8/1983 | Wilson |
| 4,906,165 A | | 3/1990 | Fox et al. |
| 5,494,530 A | * | 2/1996 | Graf .................... 134/18 |
| 5,551,462 A | | 9/1996 | Biermaier |
| 5,738,824 A | | 4/1998 | Pfeifer |
| 5,882,589 A | * | 3/1999 | Mariotti ............... 422/28 |
| 6,286,527 B1 | * | 9/2001 | Stanley ............... 134/169 C |
| 6,763,714 B2 | * | 7/2004 | Molina et al. .......... 73/302 |
| 6,764,442 B2 | * | 7/2004 | Ota et al. ............. 600/158 |
| 2004/0118413 A1 | * | 6/2004 | Williams et al. ....... 128/898 |
| 2004/0118437 A1 | * | 6/2004 | Nguyen .............. 134/22.11 |

FOREIGN PATENT DOCUMENTS

| | | |
|---|---|---|
| DE | 36 01 395 A1 | 7/1986 |
| DE | 44 34 114 A1 | 4/1995 |
| DE | 44 23 730 C2 | 1/1996 |
| DE | 299 03 174 U1 | 2/1999 |
| DE | 102 08 035 A1 | 9/2003 |
| EP | 0 072 257 A2 | 2/1983 |
| EP | 0 709 056 A1 | 5/1996 |
| EP | 0 711 529 A1 | 5/1996 |
| EP | 1 338 237 A2 | 2/2003 |
| GB | 2 275 341 A | 8/1994 |
| WO | WO91/18266 A1 | 11/1991 |

* cited by examiner

*Primary Examiner*—Linda C. M. Dvorak
*Assistant Examiner*—Matthew J. Kasztejna
(74) *Attorney, Agent, or Firm*—Senniger Powers

(57) ABSTRACT

In order to check endoscope channels, a predetermined quantity of liquid is led, at a predetermined pressure, through the channel that is to be checked, and the period of time for this is measured and evaluated. The predetermined quantity of liquid is determined via the volume of a liquid container whose outlet is capable of being connected to the channel that is to be checked. A compressed air source subjects the liquid in the container to a predetermined pressure. A sensor registers whether the liquid level in the container has dropped below a predefined value. A control unit measures the period of time within which the predetermined volume of liquid has flowed through the channel that is to be checked.

34 Claims, 4 Drawing Sheets

DEVICE FOR CHECKING ENDOSCOPE CHANNELS

FIELD OF THE INVENTION

The invention pertains to a device for checking endoscope channels.

BACKGROUND OF THE INVENTION

In the case of the machine-based cleaning, disinfection, and drying of endoscopes, one has to ensure that the very narrow endoscope channels have also been cleaned completely, and that they are not blocked wholly or partially by foreign particles that adhere to the wall of the channel.

DE 44 34 114 A1 describes a process and a device for measuring the flow resistance of a catheter in an implanted infusion system for drugs. In order to measure the patency, i.e., unobstructed flow, of the channel of the catheter, it is flushed with a predetermined volume of liquid at a predetermined pressure, whereby the period of time required for pumping this volume through the channel is measured. This predetermined volume is generated by a syringe that is capable of being hooked up to the channel of the catheter, whereby the piston of the syringe produces pressure via a spring.

EP 0 711 529 A1 describes a process and a device for checking the patency of endoscope channels. The endoscope channels are all capable of being hooked up to a common liquid container via controllable valves, whereby liquid from this container is led under pressure through the channels. The volume of liquid which flows through one or more channels per unit time is measured by means of one or more flow checking devices and compared to previous values, as a result of which it can be established whether a channel or a group of channels are patent.

It is known from DE 44 23 730 C2 that use can be made of an insertion element with controllable seals for cleaning endoscopes that have at least two channels, whereby these seals are controlled in such a way that the cleaning liquid flows through the individual channels individually. As a result of this, one ensures that the cleaning liquid flow through every channel, and that the cleaning liquid cannot drain away via other open channels if one of the channels is blocked.

In order to improve the flow through endoscope channels, U.S. Pat. No. 5,551,462 proposes an apparatus for generating increased pressure that is hooked up to the individual endoscope channels and that ensures that a cleaning liquid flows through these channels at high pressure. However, problem-free checking of the complete patency of the endoscope channels is not thereby possible.

In order to check the result after cleaning endoscopes, DE 299 03 174 U1 proposes the insertion of a test object in the machine, i.e., in addition to the endoscope, and simultaneously cleaning it and then examining the test object. If it has been cleaned in a problem-free manner, then it is assumed that the endoscope has also been cleaned in a problem-free manner. However, such an indirect test does not permit reliable conclusions to be drawn in regard to problem-free cleaning and hence in regard to the patency of the endoscope channels.

In order to measure the patency of channels, it would be possible to lead a medium under pressure (liquid or gas) through the channel and to measure the quantity of the medium flowing through the channel per unit time via a flowmeter. However, this would require very accurate flowmeters for extremely small quantities, and it is therefore technically very expensive.

Another possibility for measuring flow would comprise forcing a predetermined quantity per unit time of a medium through the channel that is to be checked, and measuring the back pressure that is produced in this way. The channel is considered to be blocked in the event of exceeding a predefined pressure value. The determination of blocking can be registered in a very simple embodiment in that a pressure producing pump becomes blocked because of the back pressure, and it then consumes a distinctly higher electric current. However, this embodiment is also very expensive or inaccurate. Both of the processes that have been described additionally require the individual connection of each individual channel to a flowmeter, a pressure meter, or a pump that are usually located in the body of the cleaning machine rather than on a support that is used for loading the machine with the endoscope. This leads, as a consequence, to the feature that every endoscope has to be connected to a corresponding number of connections, which usually amounts to between five and ten nowadays, in the washing chamber in the machine.

In general, it is also pointed out that it is not only the channels of endoscopes that can be checked with the invention but also the patency of all types of channels in items of apparatus and instruments, i.e., especially in other medical instruments as well.

SUMMARY OF THE INVENTION

The problem for the invention is to create a device for checking the unobstructed flow of endoscope channels, whereby this device ensures the reliable checking of unobstructed flow via technically simple means.

This problem is solved by the features that are indicated in Claim 1. Advantageous embodiments and developments of the invention can be seen in the dependent claims.

The basic principle of the invention comprises the feature that a liquid container with a predetermined volume and an outlet that is capable of being connected to a channel which is to be checked for open channel is assigned to each channel that is to be tested, whereby all the liquid containers are subjected to a predetermined pressure via one single common source of compressed air. A sensor registers whether the liquid level has dropped below a predefined value in one or all of the liquid containers. The period of time within which the predetermined volume has flowed through the channel/channels which is or are to be checked is measured.

BRIEF DESCRIPTION OF THE FIGURES

The invention will be described more comprehensively in the following sections by means of embodiment examples in conjunction with the drawings.

Identical reference numbers in the individual figures designate components that are identical or that correspond to one another in terms of their function.

DETAILED DESCRIPTION OF PREFERRED EMBODIMENTS

Figure 1:
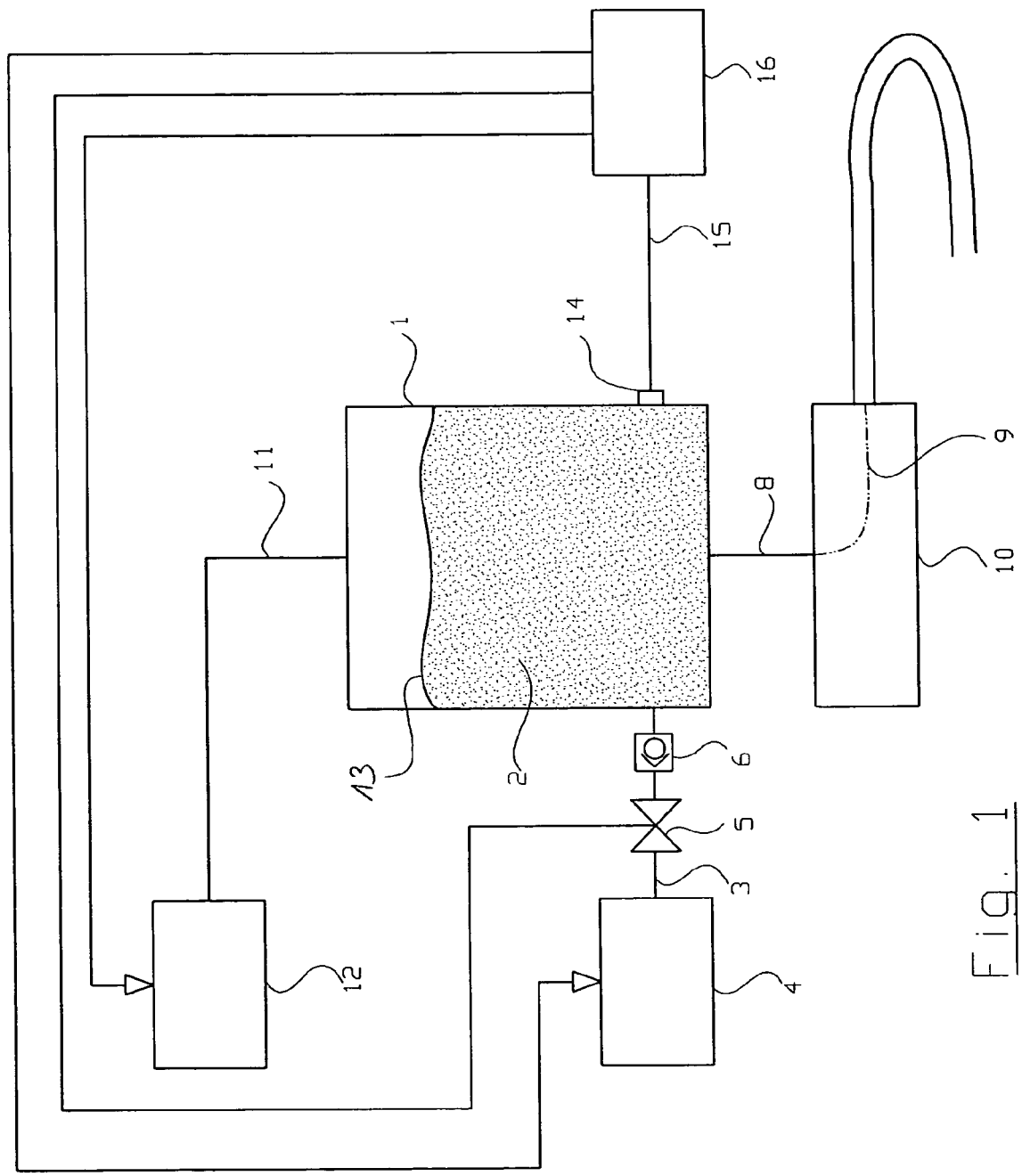
FIG. 1 shows a basic circuit diagram of a device for checking an endoscope channel.

Reference is made to FIG. 1 first of all. A container 1 with a predefined volume is shown here that is capable of being filled with a predefined quantity of a liquid 2. In order to do this, the container 1 is connected via a line 3 to a liquid supply 4, whereby the filling of the container 1 can take place via a controllable valve 5. A non-return valve 6, which prevents liquid from being able to flow back from the container 1 to the liquid supply, can also be inserted in the line 3.

An outlet is provided in the lower region of the container 1, whereby this outlet is capable of being connected via a line 8 to a channel 9 of an endoscope 10.

Furthermore, the container 1 is connected via a line 11 to a compressed air source 12, whereby the liquid 2 in the container 1 is capable of being subjected to pressure by means of this compressed air source. The line 11 preferably opens out in the upper region of the container 1, so that the surface 13 of the liquid 2 is subjected to pressure via compressed air. A sensor 14 is installed in the lower region of the container 1, whereby this sensor is connected via a line 15 to an electronic control and evaluation unit 16. This unit 16, which is designated "control unit" in the following sections, monitors the output signal from the sensor 14 and controls the compressed air source 12 and the liquid supply 4 or the valve 5.

Generally speaking, the sensor 14 has the task of establishing whether the level of the liquid 2 is below a predefined value and particularly whether container 1 has been emptied completely. In order to do this, use can be made of, e.g., known filling level indicators such as, for example, a switch that is actuated via a float, or an electronic or optical sensor that establishes the presence of a liquid. However, use can also be made of a pressure sensor as will be described more comprehensively below.

The process flow by the device that is illustrated in FIG. 1 is as follows.

In the first step, the container 1 is completely filled with liquid. In order to do this, the control unit 16 can, for example, switch on a pump, which is not illustrated, for the water supply 4, or it can open the valve 5. Air and excess liquid can escape from the container via the line 11 and the compressed air source 12.

In a second step, the liquid 2 is forced, by means of compressed air, out of the compressed air source 12 and through the endoscope channel 9 that has been hooked up. Once all the liquid 2 has been forced out of the container 1 and through the channel 9, the status "container empty" is registered by the sensor 14, and this is reported to the control unit 16. The control unit 16 hereby measures the period of time that would be necessary in order to force all the liquid out of the container 1 and through the endoscope channel 9. In the case of a known cross section of the endoscope channel 9, and a known volume of the container 1, and a known and preferably constant pressure of the compressed air source 12, the container should be completely emptied within a predefined period of time in the case where the endoscope channel 9 is free. If this is not the case, then this is a reliable sign that the endoscope channel 9 is wholly or partially blocked.

In an additional step, the container 1 is filled once again with liquid via the line 3, whereby the ventilation arrangement is shut off via the compressed air line 11 and the compressed air supply 12 so that the liquid flows directly into the channel of the endoscope and cleans or disinfects it.

In order to blow out or dry the channels, the liquid feed is switched off, e.g., by closing the valve 5, and compressed air from the compressed air source 12 is again fed to the container 1. If required, this compressed air can also be preheated. It then flows through the channel 9 of the endoscope for an additional predefined period of time, and blows out this channel and dries it. Alternatively, the air for drying purposes, which can also be preheated if required, is supplied directly via the water channel 3.

Figure 2:
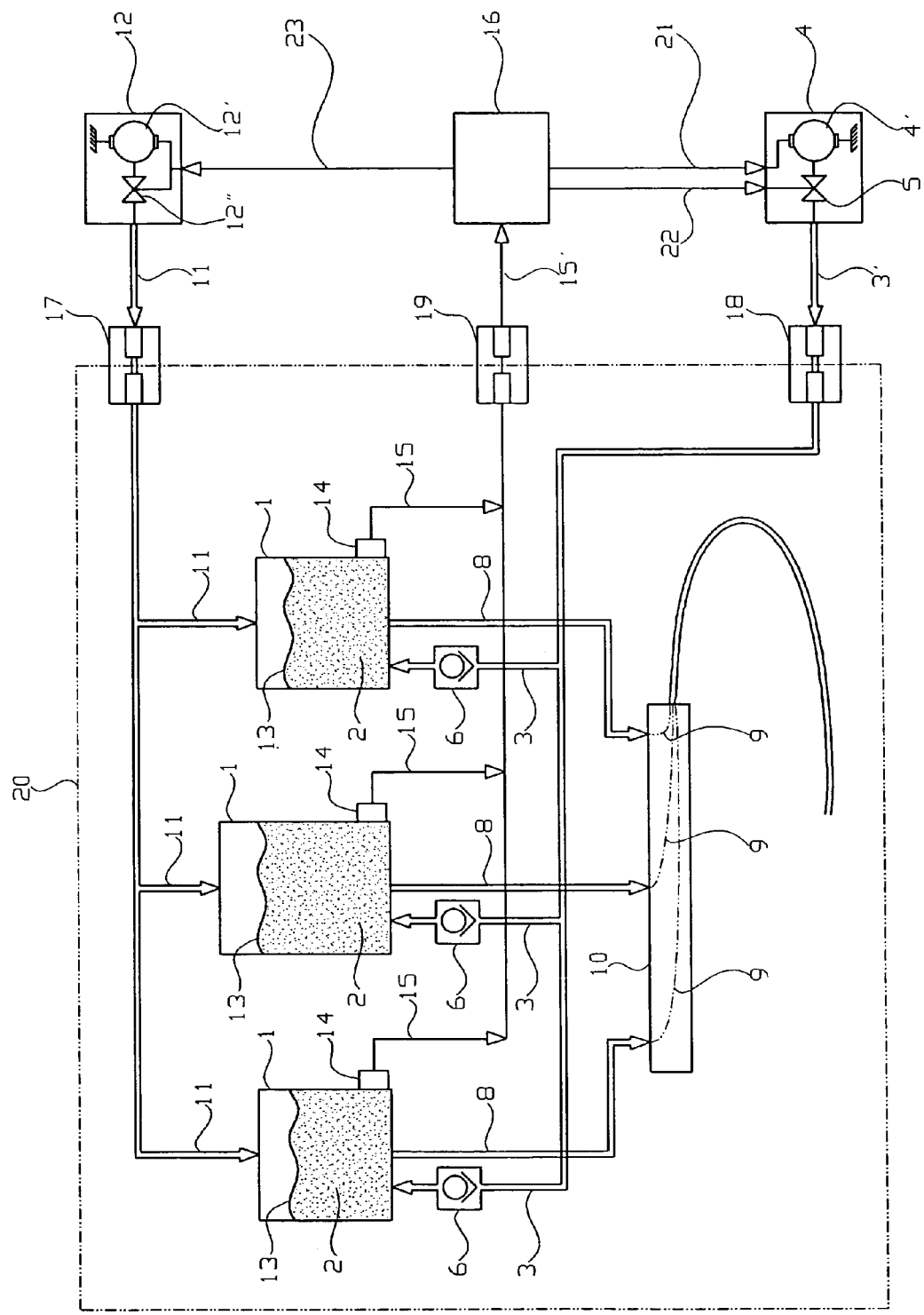
FIG. 2 shows a basic circuit diagram of a device in accordance with the invention that has been designed for checking several endoscope channels.

FIG. 2 shows an embodiment example for an endoscope 10 with three channels 9. A container 1 is assigned to each channel 9 and is hooked up to the channel 9 in question via the line 8. The endoscope 9 and all the containers 1 are arranged here on a common support 20 that can be, e.g., an insertion-type carriage that can be pushed into a cleaning and disinfection machine that is not shown. The support here has three connectors 17, 18, and 19, whereby the connector 17 connects the compressed air lines 11 to the compressed air source 12, and the connector 18 connects the liquid supply lines 3 to the liquid supply 4, and finally the connector 19 connects the lines 15 and hence the sensors 14 to the control unit 16. In accordance with the embodiment example that is shown in FIG. 1, all the containers 1 are connected in each case via a non-return valve 6 to the water supply 4, and via the lines 11 to the compressed air source 12. The control unit 16 is additionally connected to the liquid supply via electrical lines 21 and 22, whereby the liquid supply here uses, e.g., a pump 4' and the check valve 5. Furthermore, the control unit 16 is connected to the compressed air source 12 via an electrical line 23, whereby the compressed air source uses, e.g., an electrically driven compressor 12' and optionally a check valve 12" as well.

The endoscope 10 can thus be connected to the individual containers 1 outside the cleaning and disinfection machine on the support 20 via the lines 8, whereby it is pointed out here that present day endoscopes have up to ten or more channels that are to be hooked up individually. The support 20, by contrast, has to be connected only via the three connectors 17, 18, and 19 to connections in the machine, whereby this can take place either manually or via automatic connectors. The lines that are assigned to the machine are designated 3', 11', and 15'.

The mode of operation of the device in accordance with FIG. 2 corresponds completely in other regards to that which was described in connection with FIG. 1. Furthermore, it is also to be pointed out that the individual containers 1 differ in size, and thus have to be adapted to the cross sections of the channels that are to be examined. In this way, the output signals from the sensors 14 can also be combined with one another so that an endoscope is accepted as being problem-free only when all the containers with volumes which have been adapted to the channel cross section in question have been emptied in the predefined time by the compressed air at a defined pressure. It is not necessary to register or report which of the individual channels is hereby still blocked since a blocked channel will already trigger an error report.

For additional simplification, one can also proceed on the basis of defined mean cross sections for defined groups of channels, whereby this somewhat worsens the absolute accuracy of the output pronouncement "blocked" or "free," but it still gives an adequately accurate result in the case where the individual group values have been adjusted. In this way, the volumes of the containers can also be defined "by group" and they do not have to be individually adapted to each channel. In addition to this, the possibility also exists of defining individually or by group the permissible time for emptying the containers and also adapting it to the different types of endoscopes.

Figure 3:
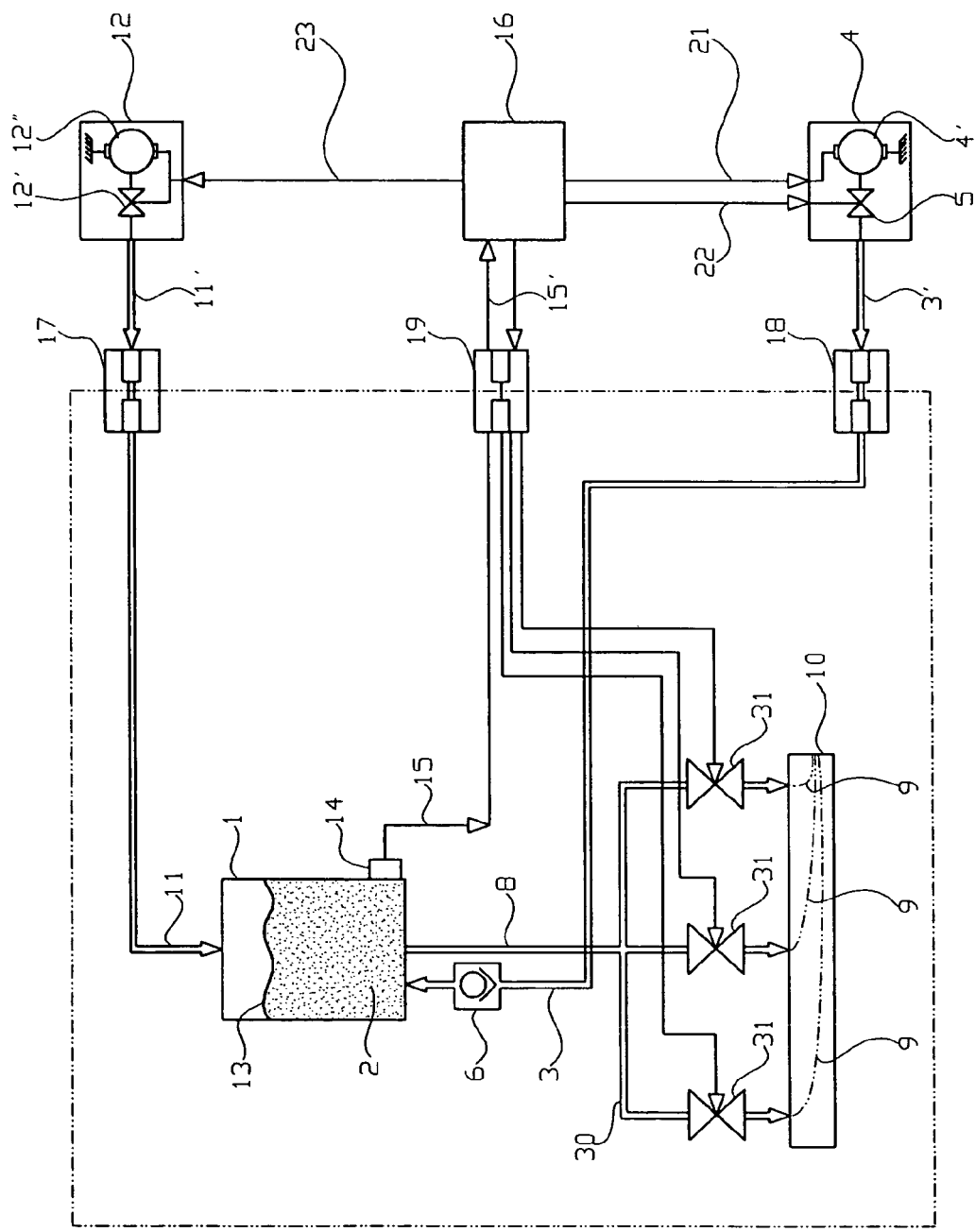
FIG. 3 shows a variant of the invention with only one container for checking several endoscope channels.

Furthermore, it may be pointed out that it is also possible to check several channels with only one container 1. In order to do this—as is shown in FIG. 3—line 8 of container 1 is connected to a branched line 30 that has multiple outlet lines that are connected individually to the individual endoscope channels via a controllable check valve 31. Then, as a function of time, the control unit 16 sequentially opens each of the valves 31 and, as a function of time, it thus sequentially effects a check of each of the individual channels. The container 1 is refilled—as described above—in each case prior to checking a channel.

Figure 4:
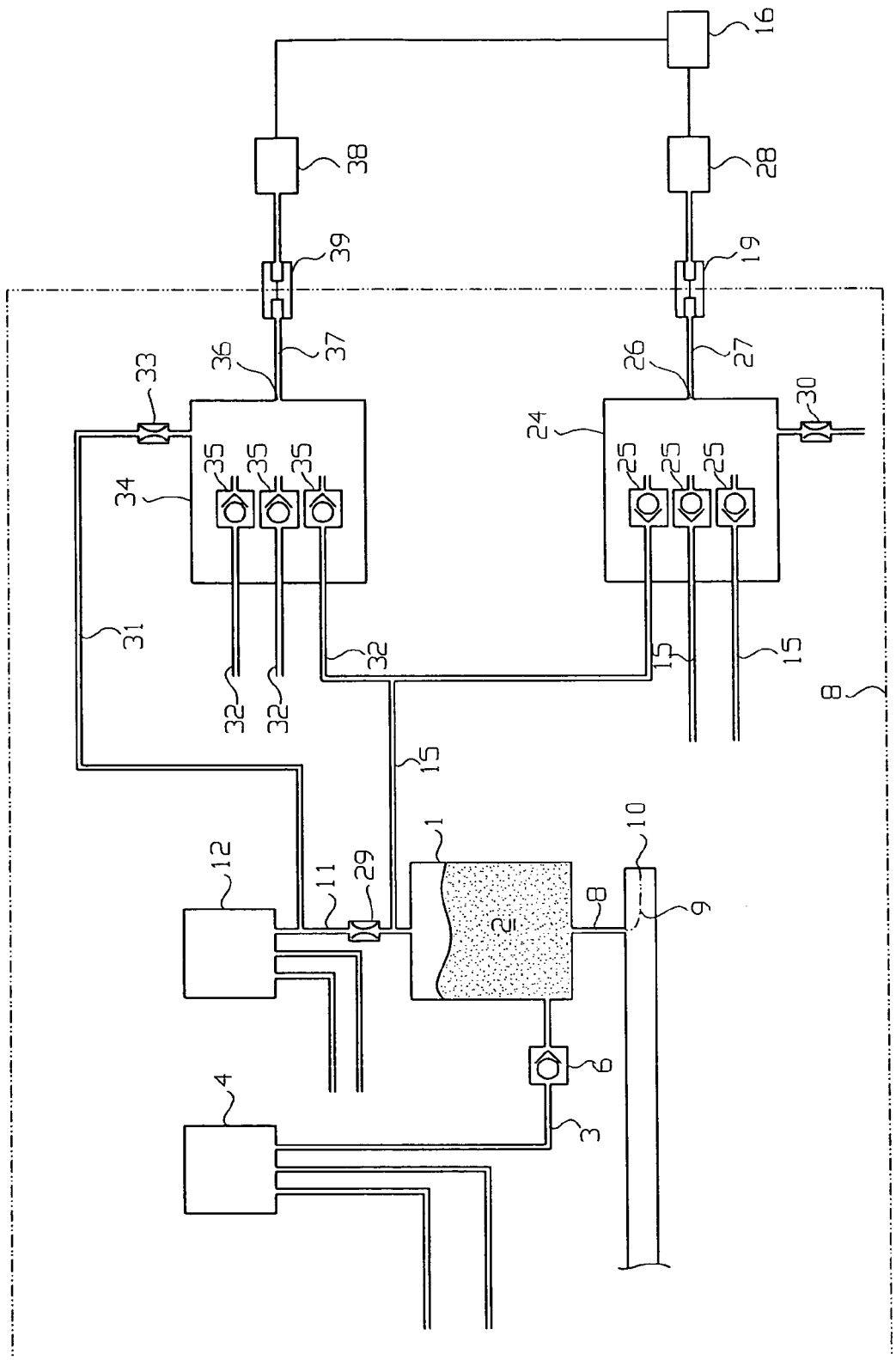
FIG. 4 shows a basic circuit diagram of the device with a pressure sensor for monitoring several containers.

FIG. 4 shows a variant of the invention in which the signal "container empty" is registered via a pressure sensor 28. A flow constriction 29, which limits the quantity of compressed air supplied and hence ensures a safe and stable pressure in the container, is arranged in the compressed air line 11 to the container 1. The pressure in the container drops at the moment in time at which the entire liquid has escaped through the channel of the endoscope; this is because the channel of the endoscope offers very much less resistance to the air now flowing through subsequently than it did beforehand to the liquid. This drop in pressure is forwarded via line 15 to an element 24 that links the sensor connections of all containers in a logic-based "OR" manner, so that the pressure at the outlet 26 of the element 24 only drops when all the inlet pressures have dropped. This output is forwarded to the pressure sensor 28 via the connector 19 of the support 20, whereby this pressure sensor forwards an electrical signal to the control unit 16. In the present embodiment example that is being illustrated, the element 24 comprises several non-return valves 25 that are in each case hooked up via line 15 or a tube to an assigned container 1 as well as to a ventilation arrangement with a small, defined cross section. The outlets of the non-return valves are mutually connected to outlet 26. The highest of the pressures generated in the lines 15 is thus forwarded to the pressure sensor 28. Because of the non-return valves however, one ensures that the higher pressure of one of the containers does not reach one of the other containers that already has a lower pressure. The pressure sensor 28 responds to the pressure drop, and reports this to the control unit 16 only when all the containers have the lower pressure.

The unit 24 is hooked up in the region of the lid of the container 1 or in line 11 after the flow constriction 29 in order that as little liquid as possible migrates in the direction of the unit 24 and impedes its functioning. The outlets of the non-return valves 25 end in an open manner in the unit 24 that here is a container whose outlet 26 has a defined cross section.

Naturally, individual pressure sensors corresponding to the sensors 14 of FIG. 1 can also be installed in each case on the containers 1, whereby the signals from these pressure sensors are led either individually or in combined form—as described previously—to the control unit 16. Furthermore, one can establish by means of the pressure sensors whether a connection 8 has been hooked up to an endoscope 10 or whether it is open, i.e., whether it has possibly been improperly connected. In order to do this, all the connections 8 of the device are connected to an outlet of defined cross section that simulates an average endoscope channel. Connections 8, which have been improperly hooked up, then lead to the situation in which the assigned container empties in a very much shorter time, whereby this is registered by the sensor 14 (FIG. 1). In this way, open connections to the connections 8 are recognized either individually or again via a combination of all signals in the form of an all-inclusive error report that notifies the user.

This function is achieved by an element 34 that is assembled in a similar manner to that of the element 24, but has a logic-based "AND" function. The inlets 32 of this element 34 are connected to the line 15 at which the inlet pressure to the container 1 prevails, namely the pressure as measured behind the flow constriction 29. Furthermore, a line 31 is hooked up to the interior of the element 34, whereby this line is connected to the pressure producer 12 or the line 11, namely in front of the flow constriction 29. A flow constriction 33 is also serially connected within the line 31. The pressure at the outlet 36 of the unit 34 thus corresponds at all times to the lowest pressure of all the inlet pressures and is led, via an additional connector 39, to an additional pressure sensor 38 and from there to the control unit 16. The unit 34 also contains non-return valves 35 that, in contrast to unit 24, are connected in the reverse direction, however. Compressed air reaches the interior of unit 34 directly from the compressed air producer 12 via the line 31 and the flow constriction 33. As long as liquid is still in the container, which is hooked up to the inlets 32, only very little compressed air flows through the non-return valves 35, especially since the supply of compressed air through the flow constriction 33 is still limited. If an endoscope channel has not been hooked up to the container 1, then the liquid that is located there escapes very rapidly and subsequently also the compressed air that is supplied subsequently from the unit 34 via the lines 32 and 15. The pressure will then drop in the interior of the unit 34, and the pressure sensor 38 (connection monitoring sensor) responds to this drop in pressure. Thus high pressure prevails at the outlet 36 of the unit 34 only when a high back pressure is still present at all the inlets 32. Thus an "AND" connection arrangement takes place in this way.

This invention is also described in German application 102 08 035.6 and European application 03 002 462.4, the entire disclosures of which are expressly incorporated herein by reference.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above methods and products without departing from the scope of the invention, it is intended that all matter contained in the above description and shown in the accompanying drawings shall be interpreted as illustrative and not in a limiting sense.

What is claimed is:

1. A device for checking unobstructed flow through separate endoscope channels of an endoscope, the device comprising:
   a plurality of liquid containers that are each assigned separately to the separate channels of the endoscope that are to be checked, whereby each liquid container has a predetermined volume and an outlet that is capable of being connected to the channel that is to be checked;

a common compressed air source to which all the liquid containers are capable of being connected and which subjects liquid in the liquid containers to a predetermined pressure;

at least one sensor that registers whether a liquid level in one or more of the liquid containers has dropped below a predefined value; and a control unit that measures the period of time within which the predetermined volume has flowed through the channel that is to be checked.

2. The device in accordance with claim 1 wherein the liquid containers and the endoscope that is to be checked are arranged on a common support, and that this support has connectors for connecting to a cleaning and disinfection machine.

3. The device in accordance with claim 2 wherein a controllable valve is serially connected within a compressed air line that connects the liquid containers to the compressed air source.

4. The device in accordance with claim 2 wherein the at least one sensor is a filling level indicator in one or more of the liquid containers.

5. The device in accordance with claim 2 wherein the at least one sensor is a pressure sensor that generates a signal "container empty" when pressure in a liquid container has dropped below a predetermined value for use in determining whether said one or more liquid containers is completely emptied within a predefined period of time for determining blockage.

6. The device in accordance with claim 5 wherein a flow constriction is provided in the compressed air line to the liquid containers.

7. The device in accordance with claim 2 wherein a common water supply is provided for filling the liquid containers.

8. The device in accordance with claim 1 wherein the liquid containers have different volumes.

9. The device in accordance with claim 8 wherein a controllable valve is serially connected within a compressed air line that connects the liquid containers to the compressed air source.

10. The device in accordance with claim 8 wherein the at least one sensor is a filling level indicator in one or more of the liquid containers.

11. The device in accordance with claim 8 wherein the at least one sensor is a pressure sensor that generates a signal "container empty" when pressure in a liquid container has dropped below a predetermined value for use in determining whether said one or more liquid containers is completely emptied within a predefined period of time for determining blockage.

12. The device in accordance with claim 11 wherein a flow constriction is provided in the compressed air line to the liquid containers.

13. The device in accordance with claim 8 wherein a common water supply is provided for filling the liquid containers.

14. The device in accordance with claim 1 wherein a controllable valve is serially connected within a compressed air line that connects the liquid containers to the compressed air source.

15. The device in accordance with claim 14 wherein the at least one sensor is a filling level indicator in one or more of the liquid containers.

16. The device in accordance with claim 14 wherein the at least one sensor is a pressure sensor that generates a signal "container empty" when pressure in a liquid container has dropped below a predetermined value for use in determining whether said one or more liquid containers is completely emptied within a predefined period of time for determining blockage.

17. The device in accordance with claim 16 wherein a flow constriction is provided in the compressed air line to the liquid containers.

18. The device in accordance with claim 14 wherein a common water supply is provided for filling the liquid containers.

19. The device in accordance with claim 18 wherein a control unit controls the water supply and the compressed air source as well as the associated valves, if required, and it monitors the at least one sensor.

20. The device in accordance with claim 1 wherein the at least one sensor is a filling level indicator in one or more of the liquid containers.

21. The device in accordance with claim 20 wherein the at least one sensor is a pressure sensor that generates a signal "container empty" when pressure in a liquid container has dropped below a predetermined value for use in determining whether said one or more liquid containers is completely emptied within a predefined period of time for determining blockage.

22. The device in accordance with claim 21 wherein a flow constriction is provided in the compressed air line to the liquid containers.

23. The device in accordance with claim 20 wherein a common water supply is provided for filling the liquid containers.

24. The device in accordance with claim 1 wherein the at least one sensor is a pressure sensor that generates a signal "container empty" when pressure in a liquid container has dropped below a predetermined value for use in determining whether said one or more liquid containers is completely emptied within a predefined period of time for determining blockage.

25. The device in accordance with claim 24 wherein a flow constriction is provided in the compressed air line to the liquid containers.

26. The device in accordance with claim 25 wherein a common pressure sensor is provided for all the liquid containers that generates the signal "container empty" only when the pressure in all the liquid containers has dropped below a predetermined value for use in determining whether said one or more liquid containers is completely emptied within a predefined period of time for determining blockage.

27. The device in accordance with claim 25 wherein a common water supply is provided for filling the liquid containers.

28. The device in accordance with claim 24 wherein a common pressure sensor is provided for all the liquid containers that generates the signal "container empty" only when the pressure in all the liquid containers has dropped below a predetermined value for use in determining whether said one or more liquid containers is completely emptied within a predefined period of time for determining blockage.

29. The device in accordance with claim 28 wherein the liquid containers are in each case all connected via non return valves to the common pressure sensor via a line and a line distributor.

30. The device in accordance with claim 24 wherein a common water supply is provided for filling the liquid containers.

31. The device in accordance with claim 1 wherein a common water supply is provided for filling the liquid containers.

32. The device in accordance with claim 31 wherein a non return valve is in each case arranged in a supply line from the common water supply to the liquid containers.

33. The device in accordance with one claim 1 wherein a connection monitoring sensor is provided that monitors whether all the liquid containers have been connected to a channel.

34. The device in accordance with claim 33 wherein the connection monitoring sensor is a pressure sensor that generates the signal "all containers connected" only when a predefined minimum pressure prevails at all the liquid containers.

* * * * *